United States Patent [19]

Sherlock et al.

[11] 3,947,588

[45] Mar. 30, 1976

[54] CYCLOPROPANE CARBOXYLIC ACID DERIVATIVES FOR LOWERING THE LEVEL OF KETONE BODIES

[75] Inventors: Margaret H. Sherlock, Bloomfield; Nathan Sperber, North Caldwell, both of N.J.

[73] Assignee: Schering Corporation, Kenilworth, N.J.

[22] Filed: Oct. 21, 1974

[21] Appl. No.: 516,327

Related U.S. Application Data

[62] Division of Ser. No. 177,871, Sept. 3, 1971, Pat. No. 3,857,880.

[52] U.S. Cl. .................................. 424/317; 424/311
[51] Int. Cl.² .......................................... A61K 31/19

[58] Field of Search ............................. 424/311, 317

[56] References Cited
UNITED STATES PATENTS

| | | | |
|---|---|---|---|
| 3,050,599 | 8/1962 | Burger | 260/515 |
| 3,674,832 | 7/1972 | Sherlock et al. | 260/515 R |

Primary Examiner—Jerome D. Goldberg
Attorney, Agent, or Firm—Bruce M. Eisen; Stephen B. Coan

[57] ABSTRACT

Disclosed herein are 2-(4-biphenyl)-cyclopropane carboxylic acids, which compounds are useful in alleviating inflammation, pain, hypoglycemia and ketosis.

5 Claims, No Drawings

CYCLOPROPANE CARBOXYLIC ACID DERIVATIVES FOR LOWERING THE LEVEL OF KETONE BODIES

This application is a division of our application Ser. No. 177,871 filed Sept. 3, 1971, and now U.S. Pat. No. 3,857,880.

This invention relates to compositions of matter which may be considered as the chemical series of 2-(4-biphenyl)cyclopropane carboxylic acid compounds and to processes for making and using such compositions.

The invention sought to be patented in one of its composition aspects is described as residing in the concept of a chemical compound having the molecular structure of cyclopropane having a carboxy moiety attached to one of the ring carbon atoms and a para-biphenyl nucleus attached to a different carbon atom of the cyclopropane ring. Each of the rings of the aforesaid biphenyl radical can optionally be further substituted. Also included within this concept are the pharmaceutically acceptable salts and esters of the aforesaid cyclopropane carboxylic acids.

The invention sought to be patented in another of its composition aspects resides in the concept of a pharmaceutical formulation having anti-inflammatory, analgesic, hypoglycemic and antiketotic properties containing a novel composition of matter of this invention.

The compositions of this invention may be represented by formula:

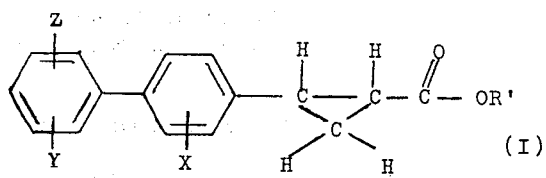

(I)

wherein X, Y and Z are independently selected from the group consisting of hydrogen, halogen, trifluoromethyl, nitro, hydroxy, lower alkyl and lower alkylthio and R' is hydrogen, an alkyl radical having 1 to 12 carbon atoms, or a pharmaceutically acceptable cation.

As used herein the term "lower alkyl" means straight chain or branched-chain radicals having up to four carbon atoms as illustrated by methyl, ethyl, isopropyl, isobutyl, and the like. X is preferably in the meta position relative to the cyclopropyl moiety and Y is preferably in the para position, particularly para-halo.

The term "pharmaceutically acceptable cation" includes any cation which forms biphenyl cyclopropane carboxylic acid salts which do not create any difference in kind of pharmaceutical activity from that shown by the corresponding free acid. Such cations can be used to provide greater solubility or greater ease in formulation than the free acid. Representative of such salts are those wherein the cation is an alkali metal such as sodium or potassium, ammonium, substituted ammonium such as diethanolammonium or such metal cations as calcium or aluminum. Similarly, the pharmaceutically acceptable esters of the free cyclopropane carboxylic acids are those which are used in pharmaceutical formulations and which do not create any difference in kind of pharmaceutical activity from that shown by the free cyclopropane carboxylic acid. The esters themselves do not change the characteristic application of the free acid but merely facilitate application or formulating of the compounds, as for example, by increasing solubility. When hydrolyzed in the body, these esters yield the free cyclopropane carboxylic acid and a pharmaceutically acceptable alcohol, e.g. ethanol. The R' moiety may be further functionally substituted to increase polarity, solubility, and other such characteristics, such R' groups including dialkylaminoalkyl (e.g. dimethylaminoethyl) and glycerol esters. Such esters are considered to be the full equivalent of the free cyclopropane carboxylic acids.

It is to be noted that formula I embraces both cis- and trans- geometric isomers as well as optical isomers. It is to be understood that this invention embraces all such isomers, although it is recognized that variations in efficacy are to be expected. Cis- and trans- isomers of the compounds of this invention can generally be separated by conventional fractional crystallization techniques or by preferential hydrolysis of the ester. Generally the trans ester hydrolyzes first and thus it can readily be separated from the cis- isomer. A desired d- or l-optical isomer can be isolated from the racemate in the conventional manner via salt formation with an optically active resolving base such as d-amphetamine. The techniques of salt formation and separation of the salts as by fractional crystallization are well known to those skilled in the art.

The compounds of formula I can be prepared by reducing an appropriately substituted acetophenone (II) with a suitable reducing agent such as sodium borohydride and then dehydrating the corresponding carbinol (III), as for example, by the use of phosphorous pentoxide or potassium bisulfate to form the corresponding styrene (IV). A reagent such as ethyl diazoacetate can then be added to product IV to form the corresponding biphenyl cyclopropane carboxylic acid ethyl ester (V). The latter ester is then hydrolyzed to the free acid (I), as for example, using potassium hydroxide. This reaction scheme can be depicted as follows:

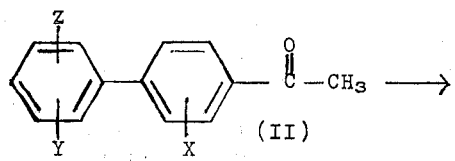

(II)

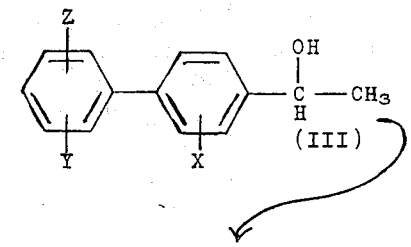

(III)

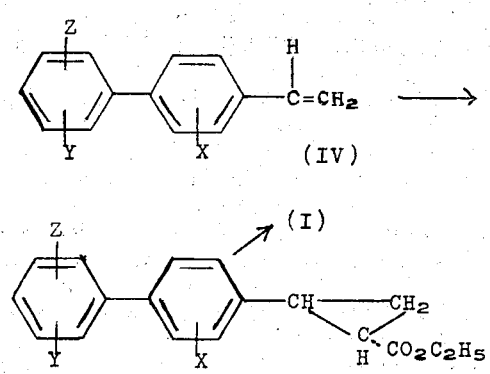

wherein X, Y and Z have the meanings described above.

The compounds of this invention may also be produced by other processes. For example, the styrene of formula IV can be oxidized using, for example, potassium permanganate and sodium iodate, to the corresponding benzaldehyde. The latter can be condensed with ethylcyanoacetate in the presence of a catalytic amount of piperidine to yield the corresponding benzal cyanoacetate. The latter can be added along with an equivalent of sodium hydride to a suspension of trimethylsulfoxonium iodide in dimethylsulfoxide. The ethyl-2-(4-biphenyl)-cyclopropane-1-cyan-1-carboxylate product is then hydrolyzed with one equivalent of potassium hydroxide in ethanol to yield the 2-(4-biphenyl)-1-carboxy-1-cyanocyclopropane. The latter is decarboxylated heating and hydrolyzed with strong base to give the desired 2-(4-biphenyl)-cyclopropane-1-carboxylic acid.

The compounds of this invention can also be produced by photolyzing the solution of the styrene of formula IV and bromomalononitrile in a suitable solvent such as methylene chloride. Cf. Boldt et al., Ber. 100, p. 1282 (1967). The product, the corresponding 2-(4-biphenyl)-1,1-dicyanopropane, can then be preferentially hydrolyzed to the mono acid and then decarboxylated under the conventional conditions to yield the corresponding cyclopropane mono nitrile which is hydrolyzed to the desired cyclopropane carboxylic acid.

In still another manner the compounds of this invention can be prepared by adding bromine to the corresponding acetophenone of formula II in ether in the presence of a catalytic amount of aluminum chloride. The resultant phenacyl bromide is then condensed with the sodium salt of ethyl cyanoacetate to yield the ethyl phenacyl cyanoacetate. The latter is then reduced to the corresponding carbinol with sodium borohydride in methanol. This carbinol can then be reacted with thionyl chloride in benzene to yield the corresponding ethyl chlorocyano acetate which can then be reacted with sodium hydride in tetrahydrofuran to effect closure of the cyclopropane ring. The resultant ethyl biphenyl cyclopropane cyanocarboxylate can then be hydrolyzed under mild conditions to the cyanocarboxylic acid. The latter is then decarboxylated and hydrolyzed to the desired free acid under strongly alkaline conditions.

EXAMPLE 1

Preparation of cis- and trans-2-(4-biphenyl)-cyclopropane carboxylic acid 14.4 g. of ethyldiazo acetate is added with stirring to a solution of 15 g. of 4-vinyl-biphenyl in 52 ml. of xylene at 90°C. over a 25 minute period. The mixture is heated to 150°C. over a 5 hour period. The cooled reaction mixture is filtered and washed with benzene. 8.7 g. of this crude cis and trans mixture of ethyl-2-(4-biphenyl)-cyclopropane carboxylate are dissolved in 80 ml. ethanol to which is added a solution of 2.65 g. of potassium hydroxide in 10.9 ml. water and the mixture is refluxed overnight. The reaction mixture is filtered and the white crystalline potassium salt is washed and dried. The salt is suspended in 1 liter of hot water and acidified. The white solid precipitate is filtered and dried overnight. A first crop is recrystallized from 300 ml. of acetonitrile and is found to be the pure trans isomer, m.p. 186°–187°C. A second crop is produced by evaporating the acetonitrile and crystallizing the residue from isopropyl ether. This product is the pure cis- isomer, m.p. 151°–153°C.

EXAMPLE 2

Preparation of cis- and trans-2-(4'chloro-4-biphenyl)-cyclopropane carboxylic acid 18 g. of 4'-chloro-4-vinyl-biphenyl is substituted in place of the 4-vinyl-biphenyl in Example 1. Following the same workup there is recovered trans-2-(4'-chloro-4-biphenyl)-cyclopropane carboxylic acid, m.p. 200°–200.5°C. and cis-2-(4'-chloro-4-biphenyl)-cyclopropane carboxylic acid, m.p. 175°–176°C.

Similarly, by substituting the corresponding substituted p-phenyl styrene analogues for p-phenylstyrene in Example 1, one can analogously prepare the corresponding cyclopropane carboxylic acids, as for example:

cis-2-(4'-fluoro-4-biphenyl)-cyclopropane carboxylic acid,
trans-2-(3-chloro-4-biphenyl)-cyclopropane carboxylic acid,
trans-2-(4'-trifluoromethyl-4-biphenyl)-cyclopropane carboxylic acid,
cis-2-(2,4'-dichloro-4-biphenyl)-cyclopropane carboxylic acid,
cis-2-(3'-hydroxy-3-thiomethyl-4-biphenyl)-carboxylic acid,
trans-2-(4'-nitro-3-bromo-4-biphenyl)-cyclopropane carboxylic acid,
cis-2-(4'-thiomethyl-4-biphenyl)-cyclopropane carboxylic acid,
cis-2-(3'-methyl-4'-chloro-2-hydroxy-4-biphenyl)-cyclopropane carboxylic acid,
trans-2-(3-nitro-4'-isobutyl-4-biphenyl)-cyclopropane carboxylic acid and,
trans-2-(2',4'-dichloro-3-methyl-4-biphenyl)-cyclopropane carboxylic acid.

The relief of inflammation by the administration of an anti-inflammatory agent without any untoward side effects being induced by this anti-inflammatory agent has long been desired. Steroids having cortisone-like activity have previously been employed to relieve inflammation. The use of steroid therapy, however, suffers from the drawback of such side effects as electrolyte imbalance, water retention and the like. The prior art has taught the use of certain non-steroidal compounds in the treatment of inflammatory conditions, but these have also been found to exhibit deleterious side effects, typically ulceration of the gastrointestinal tract. The novel compounds of this invention markedly lessen this ulcerative effect and thus they tend to exhibit high functional use indices.

It is known that the potency of a drug in delaying the appearance of edema in a rat's paw is closely correlated with its potency as an anti-inflammatory agent. Based thereon, the Carrageenin Induced Inflammation (Carrageenin Paw) Test is recognized as a standard pharmacological test for determining anti-inflammatory activity. The biphenyl cyclopropane carboxylic acids described herein exhibit an activity as evidenced by this test equal to or greater than that of the commonly used nonsteroid anti-inflammatory agent, phenylbutazone. Thus, the biphenyl cyclopropane carboxylic acids described herein are useful in treating inflammation, especially that associated with rheumatoid and osteoporosis joint diseases, collagen diseases, bursitis, gouty arthritis, spondylitis and the like.

On the basis of standard tests such as the aforesaid Carrageenin Paw Test, it is concluded that the effective anti-inflammatory dosage of the active ingredients of the compositions of this invention is within the range of about 1 to 20 mg. per kg. of mammalian body weight. These dosages can be administered once daily or can be divided and taken at given intervals during the day. In each specific instance, however, the attending diagnostician will determine the dosage, amount and frequency taking into account related health factors of the subject.

Compounds of this invention also tend to exhibit marked analgesic effects. From standard pharmacological observations such as the Mouse Antiwrithing Screen, it is concluded that the effective analgesic dosage is also within the range of about 1 to 20 mg. per kg. of mammalian body weight.

Similarly, the compounds of this invention are useful as hypoglycemic agents, that is to lower blood sugar levels. They are also useful as antiketotic agents, i.e. to lower the level of ketone bodies in the bloodstream associated with improper glucose metabolism, e.g. diabetes. Based on standard tests for such hypoglycemic and antiketotic activity, e.g. the alloxanized mouse test, the mode of administration and dosage are the same for the latter indications as for the anti-inflammatory indication.

The compounds of this invention may be administered alone or combined with other medicaments. In any event, a suitable pharmaceutically acceptable carrier is generally employed. A carrier is selected according to the route of administration to be used as well as according to the physical properties of the compounds and standard pharmaceutical practice. In a preferred embodiment the compositions of this invention are administered orally, although parenteral and topical administration are also contemplated. The preparations containing the active ingredients of this invention may be in the form of tablets, capsules, syrups, elixirs, suspensions, ointments, creams and the like.

In the formulations of pharmaceutical preparations there can be employed such substances which do not react with the compounds, as for example, water, gelatin, lactose, starches, magnesium stearate, talc, vegetable oils, benzyl alcohols, gums, polyalkylene glycols, and petroleum jelly. The following examples show typical tablet, capsule and parenteral formulations incorporating the tangible embodiments of this invention. The formulations are illustrative merely and no limitation is intended.

EXAMPLE 3

Enteric Coated Tablet Formulations

| Formula | Mg./core |
|---|---|
| Trans-2-[4-biphenyl]-cyclopropane carboxylic acid | 100.0 |
| Citric Acid | 1.0 |
| Lactose, USP | 33.5 |
| Dicalcium phosphate | 70.0 |
| Pluronic F-68 | 30.0 |
| Sodium Lauryl sulfate | 15.0 |
| Polyvinylpyrrolidone | 15.0 |
| Carbowax 1500 | 4.5 |
| Carbowax 6000 | 45.0 |
| 3A alcohol, 50 ml./1000 cores | |
| Corn starch | 30.0 |
| Dry: | |
| Sodium Lauryl sulfate | 3.0 |
| Magnesium stearate | 3.0 |
| Tablet weight | 350.0 |

Procedure - The trans-4-biphenyl-cyclopropane carboxylic acid is mixed with the citric acid, lactose, dicalcium phosphate, pluronic and sodium lauryl sulfate. The above mixture is screened through a No. 60 screen and damp granulated with an alcoholic solution consisting of polyvinylpyrrolidone, Carbowax 1500 and 6000. Add additional alcohol, if necessary, to bring powders to a pasty mass. Add corn starch and continue mixing until uniform granules are formed. Pass through a No. 10 screen, tray and dry in oven at 100°C. for 12–14 hours. Reduce dried granulation through a No. 16 screen, add sodium lauryl sulfate and magnesium sulfate, mix and compress into desired shape on a tablet machine.

Coating - The above cores are treated with a lacquer and dusted with talc to prevent moisture adsorption. Sub-coat layers are added to round out the core. A sufficient number of lacquer coats are applied to make the core enteric. Additional sub-coats and smoothing coats are applied to completely round out and smooth the tablet. Color coats are applied until desired shade is obtained. After drying the coated tablets are polished to give the tablets an even gloss.

EXAMPLE 4

Capsule Formulation

| Formula | Mg.capsule |
|---|---|
| Trans-2-(4-biphenyl)-cyclopropane carboxylic acid | 100.00 |
| Citric acid | 1.00 |
| Pluronic, F-68 | 40.00 |
| Sodium lauryl sulfate | 20.00 |
| Lactose | 238.00 |
| Magnesium stearate | 1.00 |
| | 400.00 |

Procedure - Mix together trans-[4-biphenyl]-cyclopropane carboxylic acid, citric acid, pluronic, sodium lauryl sulfate and lactose. Pass through a No. 80 screen. Add magnesium stearate, mix and encapsulate into the proper size 2 piece gelatin capsule.

EXAMPLE 5

Parenteral Suspension

| Formula | Mg. |
| --- | --- |
| Cis-2-(4'-chloro-4-biphenyl)-cyclopropane carboxylic acid microppt | 50.0 |
| Sodium citrate | 10.0 |
| Tween 80 | 1.0 |
| CMC 7 LP | 5.0 |
| Methylparaben, USP | 1.8 |
| Propylparaben, USP | .2 |
| Benzyl alcohol | 9.0 |
| Purified water ad q.s. 1 ml. | |

Sterile micro-precipitate 2-(4'-chloro-4-biphenyl)-cyclopropane carboxylic acid is dispersed in a 10X sterile filtered concentrate of Tween 80 and sodium citrate. When dispersed a 1.33X sterile filtered vehicle of the remaining components is added. When uniformly dispersed sufficient water for injection is added to final volume. The product is then stored under aseptic conditions until packaged into multiple dose vials.

Numerous variations of the above-described compositions and methods will be apparent to one skilled in the art within the spirit of the present invention.

We claim:

1. A method for lowering the level of ketone bodies in the bloodstream in a ketotic mammal comprising administering to said mammal a therapeutically effective amount for lowering the level of ketone bodies in the bloodstream in said mammal of a composition of the formula

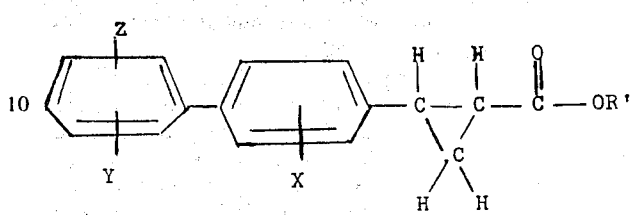

wherein X, Y and Z are independently hydrogen, halogen, trifluoromethyl, hydroxy, nitro, lower alkyl or lower alkylthio; and R' is hydrogen, an alkyl having 1 to 12 carbon atoms or a pharmaceutically acceptable cation.

2. A method according to claim 1 wherein X, Y and Z are each hydrogen.

3. A method according to claim 1 wherein Y is para-halo and X and Z are hydrogen.

4. A method according to claim 1 wherein R' is hydrogen.

5. A method according to claim 1 wherein said composition is trans-2-(4-biphenyl)-cyclopropane carboxylic acid.

* * * * *